(12) United States Patent
Majmudar et al.

(10) Patent No.: US 9,132,090 B2
(45) Date of Patent: Sep. 15, 2015

(54) PROPOFOL BASED ANESTHETIC WITH PRESERVATIVE

(76) Inventors: Chetan Majmudar, Ahmedabad (IN); Pradeep Chakravarty Mahadasyam, Ahmedabad (IN); Minesh Suthar, Ahmedabad (IN)

(*) Notice: Subject to any disclaimer, the term of this patent is extended or adjusted under 35 U.S.C. 154(b) by 911 days.

(21) Appl. No.: 13/144,092

(22) PCT Filed: Nov. 17, 2009

(86) PCT No.: PCT/IB2009/055122
§ 371 (c)(1),
(2), (4) Date: Jul. 12, 2011

(87) PCT Pub. No.: WO2010/082092
PCT Pub. Date: Jul. 22, 2010

(65) Prior Publication Data
US 2011/0275722 A1 Nov. 10, 2011

(30) Foreign Application Priority Data
Jan. 13, 2009 (IN) .............................. 91/MUM/2009

(51) Int. Cl.
*A61K 31/05* (2006.01)
*A61K 9/107* (2006.01)
*A61K 9/00* (2006.01)

(52) U.S. Cl.
CPC ............... *A61K 9/107* (2013.01); *A61K 9/0019* (2013.01)

(58) Field of Classification Search
CPC ............................... A61K 31/05; A61K 9/107
USPC .......................................................... 514/731
See application file for complete search history.

(56) References Cited

U.S. PATENT DOCUMENTS

| 4,798,846 A * | 1/1989 | Glen et al. .................... 514/731 |
| 5,696,109 A * | 12/1997 | Malfroy-Camine et al. . 514/185 |
| 5,714,520 A | 2/1998 | Jones et al. |
| 5,731,355 A | 3/1998 | Jones et al. |
| 5,731,356 A | 3/1998 | Jones et al. |
| 6,028,108 A | 2/2000 | George |
| 6,140,373 A | 10/2000 | May et al. |
| 6,140,374 A | 10/2000 | May et al. |
| 6,147,122 A | 11/2000 | Mirejovsky et al. |
| 6,150,423 A | 11/2000 | Carpenter |
| 6,177,477 B1 | 1/2001 | George et al. |
| 7,034,013 B2 * | 4/2006 | Thompson et al. ............. 514/58 |
| 2009/0131538 A1 * | 5/2009 | Goyal et al. .................. 514/731 |

* cited by examiner

*Primary Examiner* — Sreeni Padmanabhan
*Assistant Examiner* — Sahar Javanmard
(74) *Attorney, Agent, or Firm* — Harris, Shelton, Hanover & Walsh; Susan B. Fentress

(57) ABSTRACT

The invention is a sterile pharmaceutical composition for parenteral administration comprised of an oil-in-water emulsion, in which Propofol is dissolved in a water-immiscible lipophilic agents, and surface stabilizing amphiphilic agent, and tonicity modifying water-soluble hydroxy group and preservative preferably, lipophilic organic compound (butylated hydroxytoluene, butylated hydroxyanisole) or its pharmaceutically acceptable salts thereof.

8 Claims, No Drawings

PROPOFOL BASED ANESTHETIC WITH PRESERVATIVE

FIELD OF INVENTION

This invention relates to processes and compositions and methods of use of formulations containing propofol (2,6-diisopropylphenol) and one or more preservative. The present invention relates to a novel sterile pharmaceutical composition for parenteral administration containing propofol and preservative preferably, lipophilic organic compound (butylated hydroxytoluene, butylated hydroxyanisole) or its pharmaceutically acceptable salts thereof. The composition comprises an oil-in-water emulsion of propofol additionally comprising an amount of lipophilic organic compound (butylated hydroxytoluene, butylated hydroxyanisole) or its pharmaceutically acceptable salts thereof sufficient to prevent significant growth of microorganisms for at least 24 hours after, adventitious contamination. The present invention also relates to the use of the composition to induce anesthesia in mammals, including sedation, and the induction and maintenance of general anesthesia.

BACKGROUND OF THE INVENTION

Propofol (2,6-diisopropylphenol) is an injectable anesthetic, which has hypnotic properties and can be used to induce and maintain general anesthesia and sedation. Injectable anesthetics such as propofol are administered directly into the bloodstream. This results in a rapid onset of anesthesia influenced almost entirely by the rate at which the anesthetic agent crosses the blood-brain barrier. Therefore, the anesthetic agent must have sufficient lipid solubility to be able to cross this barrier and depress the relevant mechanisms of the brain. Propofol is poorly water-soluble and therefore is generally formulated as an emulsion. However, propofol containing emulsions have been shown to support microbial growth. Therefore it is desirable to formulate propofol emulsions in a manner in which microbial growth is prevented. Without a preservative in the formulation, any excess formulation must be thrown away within a few hours of its first use.

To overcome the contamination deficiencies found with propofol formulations, preservatives often added in the oil-in-water formulation to preserve its sterility and delay and retard the microorganism growth. U.S. Pat. Nos. 5,714,520, 5,731,355 and 5,731,356 disclose the use of EDTA in an amount sufficient to prevent no more than a 10-fold increase in microbial growth over 24 hours after adventitious extrinsic contamination with the microorganisms *Staphylococcus aureus* (ATCC 6538), *Escherichia coli* (ATCC 8739), *Pseudoinonas aeruginosa* (ATCC 9027) and *Candida albicans* (ATCC 10231). Disodium EDTA (ethylenediamine tetraacetate) has been shown to delay, but not prevent, the onset of microbial growth in propofol emulsions. A propofol preparation for clinical use is commercially available as DIPRIVAN 1% Injection. In this formulation, a chelating or sequestering agent (i.e., ethylene diaminetetraacetic acid (EDTA)) is included in the propofol preparation. Unfortunately, formulations containing EDTA is not truly an antimicrobial preserved product under USP standards.

U.S. Pat. No. 6,150,423 discloses using benzyl alcohol as preservative against microbial growth. U.S. Pat. Nos. 6,140,373 and 6,140,374 discloses the use of a number of antimicrobial agents in propofol containing oil-in-water emulsions including combinations of EDTA and benzyl alcohol. However, addition of benzyl alcohol destroys the oil-in-water emulsion and therefore its use is restricted to formulation having a substantially phospholipid-free emulsifying agent.

U.S. Pat. No. 6,147,122 discloses a sterile oil-in-water emulsion of propofol and an amount of sodium metabisulfite. The amount of sodium metabisulfite in propofol administrated to patients requires careful monitoring not to exceed the limit set by the World Health Organization (WHO) (7.0 mg/kg as SO2) and the amount infused in total-parenteral-nutrition amino acid formulations, as well as during peritoneal dialysis. In addition, sodium metabisulfite is known for its potential allergy and hypersensitivity in some patients.

U.S. Pat. No. 6,028,108 discloses a sterile oil-in-water emulsion of propofol and an amount of pentetate sufficient to prevent significant growth of microorganisms for at least 24 hours after adventitious extrinsic contamination. U.S. Pat. No. 6,177,477 discloses a sterile oil-in-water emulsion of propofol and an amount of tromethamine (T1US) sufficient to prevent significant growth of microorganisms for at least 24 hours after adventitious extrinsic contamination.

There is a continuing need to find a suitable preservative for use in the oil-in-water emulsion containing propofol. We surprisingly discovered inclusion of an amount of lipophilic organic compound (butylated hydroxytoluene, butylated hydroxyanisole) or its pharmaceutically acceptable salts thereof in a propofol oil-in-water emulsion is highly effective in preventing significant growth of a wide range of different microorganisms, including Gram (+) and Gram (−) bacteria as well as yeast and fungi, for at least 24 hours after adventitious contamination.

Many compounds varying dramatically in structure are known to serve as conventional preservatives. Depending upon the intended application or use of a product, a particular preservative is generally preferred. For example, conventional preservatives for food use are generally different than preservatives for cosmetic use, which in turn are generally different than preservatives for pharmaceutical use. Exemplary conventional preservatives include benzalkonium chloride, benzethonium chloride, benzoic acid, chlorobutanol, chlorocresol, methyl, ethyl and phenol, phenoxyethanol, propyl gallate, sorbic acid, benzyl alcohol, EDTA, pentetate, abide, organic solvent (such as glycol, propylene glycol, or polyethylene glycol), peroxide, ozone, chlorite, sodium bisulfite, potassium metabisulfite, potassium sulfite, sodium sulfite, and others known to those of ordinary skill in the art.

SUMMARY OF INVENTION

The present invention is directed to a sterile pharmaceutical composition comprising oil-in-water emulsion formulation having as preservative preferably, lipophilic organic compound (butylated hydroxytoluene, butylated hydroxyanisole) or its pharmaceutically acceptable salts thereof. The term "preservative" means an agent which delays onset or retards rate of growth to less than 1 logarithmic increase over a 24 hour period as compared to an unpreserved formulation.

The invention is a sterile pharmaceutical composition for parenteral administration comprised of an oil-in-water emulsion, in which Propofol is dissolved in a water-immiscible lipophilic agents, preferably soybean oil, and surface stabilizing amphiphilic agent, preferably egg lecithin and tonicity modifying water-soluble hydroxy group preferably glycerol and preservative preferably, lipophilic organic compound (butylated hydroxytoluene, butylated hydroxyanisole) or its pharmaceutically acceptable salts thereof.

DETAILED DESCRIPTION OF THE INVENTION

The compound 2,6-diisopropylphenol (propofol) is a well-known anesthetic agent. The onset of anesthesia is largely controlled by a drug's diffusion rate through the blood-brain barrier. Propofol is lipophilic and this helps the compound to provide rapid anesthetic action. However, this lipophilicity renders propofol, a liquid at room temperature, relatively insoluble in water. As a result, propofol is commonly administered (directly into the bloodstream either by infusion or by bolus injection) as an oil-in-water emulsion, containing a lipid component. Lipids, however, are good substrates for bacterial growth and, bacterial growth can be delay and retard with preservatives preferably, lipophilic organic compound (butylated hydroxytoluene, butylated hydroxyanisole) or its pharmaceutically acceptable salts thereof.

An oil-in-water emulsion is meant to be a distinct, two-phase system that is in equilibrium and in effect, as a whole, is kinetically stable and thermodynamically unstable. Typically the lipophilic agent is oil such as soybean oil, sunflower oil, castor oil, cottonseed oil, corn oil, coconut oil, arachis oil, marine oils or olive oil and mixture thereof. Preferably the oil is soybean oil. Suitable tonicity modifying water-soluble hydroxy group is selected from a monosaccharide, a disaccharide, a trisaccharide, sucrose, dextrose, trehalose, mannitol, lactose, glycerol, glycerin, sorbitol, and mixtures thereof. Propofol dissolved in the water immiscible lipophilic agents, is emulsified in aqueous medium with the aid of a surface stabilizing amphiphilic agent. Suitable surface stabilizing amphiphilic agent include for example egg lecithin, egg phosphatidylcholine, soy lecithin, soy phosphatidylcholine, 1,2-dimyristoyl-sn-glycero-3-phosphotidlycholine (DMPC), 1,2-dimyristoyl-sn-glycero-3-[phospho-rac-(1-glycerol)] (DMPG), L-alpha-phosphatidylcholine, palmitoyl-linoleoyl phosphatidylcholine, stearoyl-linoleoyl phosphatidylcholine, lysolecithin, phosphatidic acid, phosphatidyl-DL-glycerol, phosphatidylethanolamine, palmitoyl-oleoyl phosphatidylcholine, phosphatidylinositol, phosphatidylserine, 1,3-bis (sn-3-phosphatidyl)-sn-glycerol, 1,3-di(3-sn-phosphatidyl)-sn-glycerol, and mixtures thereof. Preferably, the surface stabilizing amphiphilic agent is egg lecithin. The formulation of the present invention typically comprises from 0.1% to 10% by weight of Propofol.

Propofol is a liquid that is very poorly soluble in water. To manufacture stable injectable propofol formulations with the desired anti-microbial properties, lipid content and with little or no phase separation of the propofol during mixing or storage, it was found necessary to not only select an appropriate composition of the formulation but also use appropriate processing conditions. Examples of suitable processing conditions are those, which provide intense mechanical agitation or high sheer. The formulation is conveniently prepared by the initial preparation of a aqueous phase, oil phase, which are then mixed and homogenization.

Aqueous Phase Preparation

Water for injection, tonicity modifying water-soluble hydroxy group, and ampiphilic agents were mixed to prepare the aqueous Phase. The dissolution process was accelerated by heating the mixture while mixing with a high-speed mixture vessel to 4000 rpm and maintain the flow rate of 3000 L/Hr. The aqueous phase was usually a mixture of polyhydroxy compounds in water and in some cases also contained well-dispersed phospholipid prepared using a high-speed mixture vessel.

Oil Phase Preparation

Propofol, lipophilic agents, and preservative preferably, lipophilic organic compound (butylated hydroxytoluene, butylated hydroxyanisole) or its pharmaceutically acceptable salts thereof are mixed to prepare the Oil phase. Adding of Propofol to lipophilic agent with caution, and mix it for 30-40 minutes.

The mixing was prepared by adding the Oil phase to the aqueous phase under agitation with a high-speed mixture vessel. Maintain the speed of mixture vessel to 4200 rpm. after the completion of oil phase addition to aqueous phase keep re-circulation of formed emulsion till the globule size of emulsion reduces.

Homogenization

The dispersions of the water insoluble matrix in aqueous medium were prepared by either of several homogenization methods. For example, dispersions were prepared by high-pressure homogenization of the mixed emulsion. The temperature of the process-fluid rises rapidly because of homogenization at a high pressure. In some cases high-pressure homogenization at high temperatures resulted in dispersion with a tendency to suffer from phase separation. Therefore, the effluent of the homogenizer was cooled by heat exchanger, to maintain an acceptable temperature at the inlet of the homogenizer. After the homogenization phase is over adjust the pH about 8.9 to 9.2 with sodium hydroxide solution and start the final stage of homogenization.

Packaging and Sterilization

The aqueous dispersion prepared by one of the above processes was filled into glass vials to about 70-90% volume capacity, purged with a generally inert atmosphere, for example nitrogen, and sealed with compatible stoppers and seals. The packaged novel propofol formulations were found generally to be stable pharmaceutically acceptable steam sterilization cycles.

In the preferred embodiment lipophilic agents is an oil such as soybean oil, sunflower oil, castor oil, cottonseed oil, corn oil, coconut oil, arachis oil, marine oils or olive oil alternatively the lipophilic agents can be an ester of a medium or long chain fatty acid, for example triglyceride or a compound such as glycerol ester or polyoxyl hydrogenated castor oil, isopropyl myristate, ethyl oleate, capriccaprylic triglyceride and mixture thereof.

In the preferred embodiment amphiphilic agent is selected from the group consisting of egg lecithin, egg phosphatidylcholine, soy lecithin, soy phosphatidylcholine, 1,2-dimyristoyl-sn-glycero-3-phosphotidlycholine (DMPC), 1,2-dimyristoyl-sn-glycero-3-[phospho-rac-(1-glycerol)] (DMPG), L-alpha-phosphatidylcholine, palmitoyl-linoleoyl phosphatidylcholine, stearoyl-linoleoyl phosphatidylcholine, lysolecithin, phosphatidic acid, phosphatidyl-DL-glycerol, phosphatidylethanolamine, palmitoyl-oleoyl phosphatidylcholine, phosphatidylinositol, phosphatidylserine, 1,3-bis (sn-3-phosphatidyl)-sn-glycerol, 1,3-di(3-sn-phosphatidyl)-sn-glycerol, and mixtures thereof.

In the preferred embodiment tonicity modifying water-soluble hydroxy group excipient is selected from the group consisting of a monosaccharide, a disaccharide, a trisaccharide, sucrose, dextrose, trehalose, mannitol, lactose, glycerol, glycerin, sorbitol, and mixtures thereof.

Present Invention is as Below

TABLE 1

| Component | Range (Weight %) | Preferred Amount (Weight %) |
| --- | --- | --- |
| Propofol | 1.0-10.0 | 1 |
| Soybean oil | 5.0-20.0 | 10 |
| Egg Lecithin | 0.5-2.0 | 1.2 |
| Glycerol | 2.0-3.0 | 2.25 |
| Butylated Hydroxy anisole | 0.00001-0.001 | 0.0001 |
| Butylated hydroxytoluene | 0.00001-0.001 | 0.0001 |
| Sodium Hydroxide | q.s | q.s |
| Water for Injection | to 100 | to 100 |

The following examples are intended to be illustrative for the present invention and should not be construed as limiting the scope of this invention defined by the appended example

Example 1

Weigh accurately required quantity of 10.00 gm Propofol, 96.00 gm Refined Soya Oil, 0.001 gm BHA (0.001 mg/ml) and 0.001 gm BHT (0.001 mg/ml) solution and 12.00 gm Egg lecithin, in a clean dry beaker and mix it on magnetic stirrer at 60° C. until all ingredients gets dissolved. In parallel to above aqueous phase is prepared take 22.50 gm Glycerol and 600 ml Water for Injection in clean dry beaker, with constant stirring on magnetic stirrer at 55° C. After complete dissolving oil phase add this solution in aqueous phase. Slowly with continuous stirring temperature maintain 60° C. (Stirring 1 hr.) make up the volume of the batch size 1000 ml with water for injection. Homogenize the solution until required globule size is achieved. After homogenization check the globule size and pH of the solution. Adjust the pH of the solution to 8.90-9.20 with 0.1N sodium hydroxide. Then fill the solution in previously washed, dried USP type-I glass vials. Purge the solution with Nitrogen gas Seal it with gray-colored rubber closure and flip off seal. Sterilized the sample by Autoclave.

Example 2

Weigh accurately required quantity of 10.00 gm Propofol, 98.00 gm Refined Soya Oil, 0.001 gm BHA (0.001 mg/ml) solution and 12.00 gm Egg lecithin, in a clean dry beaker and mix it on magnetic stirrer at 60° C. until all ingredients gets dissolved. In parallel to above aqueous phase is prepared take 22.50 gm Glycerol and 600 ml Water for Injection in clean dry beaker, with constant stirring on magnetic stirrer at 55° C. After complete dissolving oil phase add this solution in aqueous phase. Slowly with continuous stirring temperature maintain 60° C. (Stirring 1 hr.) make up the volume of the batch size 1000 ml with water for injection. Homogenize the solution until required globule size is achieved. After homogenization check the globule size and pH of the solution. Adjust the pH of the solution to 8.90-9.20 with 0.1N sodium hydroxide. Then fill the solution in previously washed, dried USP type-I glass vials. Purge the solution with Nitrogen gas. Seal it with gray-colored rubber closure and flip off seal. Sterilized the sample by Autoclave.

Example 3

Weigh accurately required quantity of 10.00 gm Propofol, 98.00 gm Refined Soya Oil, 0.001 gm BHT (0.001 mg/ml) solution and 12.00 gm Egg lecithin, in a clean dry beaker and mix it on magnetic stirrer at 60° C. until all ingredients gets dissolved. In parallel to above aqueous phase is prepared take 22.50 gm Glycerol and 600 ml Water for Injection in clean dry beaker, with constant stirring on magnetic stirrer at 55° C. After complete dissolving oil phase add this solution in aqueous phase. Slowly with continuous stirring temperature maintain 60° C. (Stirring 1 hr.) make up the volume of the batch size 1000 ml with water for injection. Homogenize the solution until required globule size is achieved. After homogenization check the globule size and pH of the solution. Adjust the pH of the solution to 8.90-9.20 with 0.1N sodium hydroxide. Then fill the solution in previously washed, dried USP type-I glass vials. Purge the solution with Nitrogen gas. Seal it with gray-colored rubber closure and flip off seal. Sterilized the sample by Autoclave.

In the preferred embodiment propofol oil-in-water emulsions containing 0.00002% BHT, 0.00002% BHT/0.000005% BHA, 0.00001% BHT/0.0000025 BHA, 0.000006% BHT/0.0000015% BHA and 0.00001% BHA were tested by the USP preservative efficacy test as described in United States Pharmacopoeia. Briefly, this involves inoculating the test solution with $10^5$ to $10^6$ test organisms per milliliter and then determining the number of surviving organisms after 6, 12, 18, and 24 hrs incubation at 20-25° C. using standard microbiological methods. The USP test organisms include the bacteria *Staphylococcus aureus, Escherichia coli,* and *Pseudomonas aeruginosa*, yeast (*Candida albicans*), and mold (*Aspergillums niger*). In order to meet the criteria of the USP preservative efficacy test, the bacteria must demonstrate not less than 1.0 log reduction from initial count and no increase of Yeast and Molds from the initial calculated count. The initial inoculums level can either be calculated knowing the stock culture concentration or by using a buffer control instead of the test solution. The results, using formulations, which are Propofol 1% fat emulsions, are given below in Tables 2-6.

TABLE 2

PROPOFOL WITH BHT
Preservative: BHT: 0.00002%,
Initial Strength $10^5$

| Time | E. Coli | S. Aureus | P. Aeruginosa | A. Niger | C. Albicans |
|---|---|---|---|---|---|
| Initial | $2.7 \times 10^5$ | $2.6 \times 10^5$ | $2.5 \times 10^5$ | $2.4 \times 10^5$ | $3.3 \times 10^5$ |
| 6 hrs | $2.9 \times 10^3$ | $2.6 \times 10^4$ | $2.8 \times 10^3$ | $2.6 \times 10^4$ | $2.9 \times 10^4$ |
| 12 hrs | $3.1 \times 10^2$ | $3.2 \times 10^3$ | $2.9 \times 10^2$ | $2.5 \times 10^3$ | $3.5 \times 10^3$ |
| 18 hrs | $2.6 \times 10^2$ | $2.9 \times 10^3$ | $2.6 \times 10^2$ | $2.0 \times 10^3$ | $2.7 \times 10^3$ |
| 24 hrs | $2.4 \times 10^2$ | $2.6 \times 10^3$ | $2.1 \times 10^2$ | $1.8 \times 10^3$ | $2.4 \times 10^3$ |
| Log reduction | 3 | 2 | 3 | 2 | 2 |

TABLE 3

PROPOFOL WITH BHT-BHA
Preservative: BHT: 0.00002%, BHA: 0.000005%
Initial Strength $10^5$

| Time | E. Coli | S. Aureus | P. Aeruginosa | A. Niger | C. Albicans |
|---|---|---|---|---|---|
| Initial | $2.7 \times 10^5$ | $2.6 \times 10^5$ | $2.5 \times 10^5$ | $2.4 \times 10^5$ | $3.3 \times 10^5$ |
| 6 hrs | $2.3 \times 10^2$ | $3.3 \times 10^4$ | $6.3 \times 10^3$ | $4.1 \times 10^4$ | $6.9 \times 10^4$ |
| 12 hrs | $2.9 \times 10^1$ | $4.1 \times 10^3$ | $7.9 \times 10^2$ | $3.3 \times 10^3$ | $1.9 \times 10^3$ |
| 18 hrs | $2.3 \times 10^1$ | $2.0 \times 10^3$ | $6.6 \times 10^2$ | $2.6 \times 10^3$ | $1.2 \times 10^3$ |
| 24 hrs | $1.0 \times 10^1$ | $1.9 \times 10^3$ | $4.0 \times 10^2$ | $2.2 \times 10^3$ | $0.6 \times 10^3$ |
| Log reduction | 4 | 3 | 3 | 2 | 3 |

TABLE 4

PROPOFOL WITH BHT-BHA
Preservative: BHT: 0.00001%, BHA: 0.0000025%
Initial Strength $10^5$

| Time | E. Coli | S. Aureus | P. Aeruginosa | A. Niger | C. Albicans |
|---|---|---|---|---|---|
| Initial | $2.7 \times 10^5$ | $2.6 \times 10^5$ | $2.5 \times 10^5$ | $2.4 \times 10^5$ | $3.3 \times 10^5$ |
| 6 hrs | $5.0 \times 10^3$ | $8.0 \times 10^1$ | $3.9 \times 10^3$ | $7.0 \times 10^4$ | $4.9 \times 10^3$ |
| 12 hrs | $6.1 \times 10^2$ | $9.0 \times 10^1$ | $5.2 \times 10^2$ | $8.0 \times 10^3$ | $7.2 \times 10^2$ |
| 18 hrs | $4.9 \times 10^2$ | $8.3 \times 10^1$ | $4.4 \times 10^2$ | $6.4 \times 10^3$ | $6.1 \times 10^2$ |
| 24 hrs | $3.3 \times 10^2$ | $6.6 \times 10^1$ | $3.2 \times 10^2$ | $4.0 \times 10^3$ | $5.3 \times 10^2$ |
| Log reduction | 3 | 4 | 3 | 2 | 3 |

TABLE 5

PROPOFOL WITH BHT-BHA
Preservative: BHT: 0.000006%, BHA: 0.0000015%
Initial Strength $10^5$

| Time | E. Coli | S. Aureus | P. Aeruginosa | A. Niger | C. Albicans |
|---|---|---|---|---|---|
| Initial | $2.7 \times 10^5$ | $2.6 \times 10^5$ | $2.5 \times 10^5$ | $2.4 \times 10^5$ | $3.3 \times 10^5$ |
| 6 hrs | $2.8 \times 10^3$ | $2.7 \times 10^3$ | $2.8 \times 10^3$ | $2.7 \times 10^4$ | $2.9 \times 10^4$ |
| 12 hrs | $3.1 \times 10^2$ | $2.9 \times 10^2$ | $2.5 \times 10^2$ | $3.0 \times 10^3$ | $3.4 \times 10^3$ |
| 18 hrs | $2.8 \times 10^2$ | $2.4 \times 10^2$ | $2.1 \times 10^2$ | $2.8 \times 10^3$ | $3.0 \times 10^3$ |
| 24 hrs | $2.6 \times 10^2$ | $1.9 \times 10^2$ | $1.6 \times 10^2$ | $2.4 \times 10^3$ | $2.6 \times 10^3$ |
| Log reduction | 3 | 3 | 3 | 2 | 2 |

TABLE 6

PROPOFOL WITH BHA
Preservative: BHA: 0.0001%
Initial Strength $10^6$

| Time | E. Coli | S. Aureus | P. Aeruginosa | A. Niger | C. Albicans |
|---|---|---|---|---|---|
| 6 hrs | $3.0 \times 10^5$ | $4.3 \times 10^5$ | $3.0 \times 10^4$ | $3.0 \times 10^5$ | $3.0 \times 10^5$ |
| 12 hrs | $2.9 \times 10^5$ | $3.3 \times 10^5$ | $3.3 \times 10^3$ | $2.6 \times 10^5$ | $3.1 \times 10^4$ |
| 18 hrs | $3.9 \times 10^4$ | $3.9 \times 10^4$ | $2.6 \times 10^3$ | $2.2 \times 10^5$ | $2.3 \times 10^4$ |
| 24 hrs | $3.0 \times 10^4$ | $2.5 \times 10^4$ | $1.4 \times 10^3$ | $1.7 \times 10^5$ | $1.0 \times 10^4$ |
| Log reduction | 2 | 2 | 3 | 1 | 2 |

We claim:

1. A sterile pharmaceutical anesthetic composition comprising: an oil-in-water emulsion with from 1 to 10 weight percent of propofol; from 5 to 20 weight % of a lipophilic agent; from 0.5 to 2.0 weight % of a surface stabilizing amphiphilic agent; from 2.0 to 3.0 weight % of a tonicity modifying water-soluble hydroxyl group; from 0.00001 to 0.001 weight % of a preservative selected from the group consisting of: butylated hydroxytoluene and butylated hydroxyanisole or a mixture thereof.

2. A sterile pharmaceutical anesthetic composition of claim 1, wherein said lipophilic agent is an ester of a medium or long chain fatty acid, and is selected from the group consisting of triglyceride derivatives, glycerol ester or polyoxyl hydrogenated castor oil, isopropyl myristate, ethyl oleate, and capriccaprylic triglyceride or a mixture thereof.

3. A sterile pharmaceutical anesthetic composition of claim 1, wherein said lipophilic agent is an oil and is selected from the group consisting of soybean oil, sunflower oil, castor oil, cottonseed oil, corn oil, coconut oil, arachis oil, marine oils and olive oil or a mixture thereof.

4. A sterile pharmaceutical anesthetic composition of claim 1, wherein said lipophilic agent is soybean oil.

5. A sterile pharmaceutical anesthetic composition of claim 1, wherein said tonicity modifying water-soluble hydroxyl group is selected from the group consisting of a monosaccharide, a disaccharide, a trisaccharide, sucrose, dextrose, trehalose, mannitol, lactose, glycerol, glycerin, and sorbitol, or a mixture thereof.

6. A sterile pharmaceutical anesthetic composition of claim 1, wherein said tonicity modifying water-soluble hydroxyl is glycerol.

7. A sterile pharmaceutical anesthetic composition of claim 1, wherein said surface stabilizing amphiphilic agent is selected from the group consisting of egg lecithin, egg phosphatidylcholine, soy lecithin, soy phosphatidylcholine, 1,2-dimyristoyl-sn-glycero-3-phosphotidlycho line (DMPC), 1,2-dimyristoly-sn-glycero-3-[phosphor-rac-(1-glycerol)] (DMPG), L-alpha-phosphatidylcholine, palmitoyl-linoleoyl phosphatidylcholine, stearoyl-linoleoyl phosphatidylcholine, lysolecithin, phosphatidic acid, phosphatidyl-DL-glycerol, phosphatidylethanolamine, palmitoyl-oleoyl phosphatidylcholine, phosphatidylinositol, phosphatidylserine, 1,2-bis (sn-3-phosphadidyl)-sn-glycerol, and 1,3-di(3-sn-phosphatidyl)-sn-glycerol or a mixture thereof.

8. A sterile pharmaceutical anesthetic composition of claim 1, wherein said surface stabilizing amphiphilic agent is egg lecithin.

* * * * *